United States Patent [19]
Buysse et al.

[11] Patent Number: 5,776,130
[45] Date of Patent: Jul. 7, 1998

[54] VASCULAR TISSUE SEALING PRESSURE CONTROL

[75] Inventors: Steven P. Buysse, Longmont; Jenifer S. Kennedy, Boulder; Michael J. Lands, Louisville; Donald R. Loeffler, Longmont; S. Wade Lukianow, Boulder; Thomas P. Ryan, Fort Collins, all of Colo.

[73] Assignee: Valleylab, Inc., Boulder, Colo.

[21] Appl. No.: 530,450

[22] Filed: Sep. 19, 1995

[51] Int. Cl.⁶ .................................................. A61B 17/36
[52] U.S. Cl. .............................. 606/48; 606/50; 606/51
[58] Field of Search .......................... 606/32, 38, 41, 606/42, 48, 191, 213, 215, 216, 50–52, 118, 151, 142, 143; 607/115, 116; 128/736, 734

[56] References Cited

U.S. PATENT DOCUMENTS

| | | | |
|---|---|---|---|
| 3,780,416 | 12/1973 | Rider | 606/143 |
| 4,043,342 | 8/1977 | Morrison, Jr. | |
| 4,279,257 | 7/1981 | Hochstein | 128/722 |
| 4,293,961 | 10/1981 | Runge | 600/14 |
| 4,387,714 | 6/1983 | Geddes et al. | 606/32 |
| 4,637,392 | 1/1987 | Sorochenko | 606/50 |
| 4,644,950 | 2/1987 | Valli | 606/46 |
| 5,007,908 | 4/1991 | Rydell | |
| 5,016,521 | 5/1991 | Haka | 92/13.1 |
| 5,047,027 | 9/1991 | Rydell | |
| 5,061,269 | 10/1991 | Muller | 606/151 |
| 5,127,412 | 7/1992 | Casmetto et al. | 128/898 |
| 5,282,800 | 2/1994 | Foshee et al. | 606/41 |
| 5,290,286 | 3/1994 | Parins | |
| 5,314,424 | 5/1994 | Nicholas | 606/41 |
| 5,334,193 | 8/1994 | Nardella | 606/41 |
| 5,342,357 | 8/1994 | Nardella | |
| 5,354,296 | 10/1994 | Turkel | 606/41 |
| 5,456,684 | 10/1995 | Schmidt et al. | 606/41 |
| 5,527,313 | 6/1996 | Scott et al. | 606/41 |
| 5,540,684 | 7/1996 | Hassler, Jr. | 606/38 |
| 5,542,945 | 8/1996 | Fritzsch | 606/50 |

FOREIGN PATENT DOCUMENTS

| | | |
|---|---|---|
| 9206642 | 4/1992 | European Pat. Off. |
| WO 9313719 | 7/1993 | WIPO |

Primary Examiner—Jennifer Bahr
Assistant Examiner—Rosiland Kearney

[57] ABSTRACT

A clamping force mechanism for use with electrosurgery allow a user to seal and/or join patient's particular vascular tissue; the mechanism is elongate with user and patient ends. An actuator is at the user end and the effectors are at the patient end. Each effector has a face of an area to contact the particular vascular tissue. A lost motion connection transfers user actuation to the effectors to hold a predetermined clamping force during electrosurgical tissue sealing. A yielding member in the loss motion connection clamps the particular tissue between the faces with a predetermined force. The yielding member is a spring, slip clutch or hydraulic coupling possibly near the actuator. An active electrode is carried on one end effector and a return electrode contacts the tissue so an electrosurgical energy supply connected thereacross delivers energy therebetween. A feedback circuit responds to parameters of energy delivered to tissue. A temperature sensor on one face and an impedance monitor respond to energy delivered. A control applies energy to held tissue to seal and/or join it.

17 Claims, 6 Drawing Sheets

5,776,130

VASCULAR TISSUE SEALING PRESSURE CONTROL

FIELD OF THE INVENTION

A clamping force mechanism for an instrument allows a user to apply force within an preferred range to hold particular vascular tissue of a patient during application of electrosurgical energy to seal and /or join the particular tissue.

BACKGROUND OF THE DISCLOSURE

Sealing and/or joining of particular vascular tissue during surgery is an essential part of an operation or procedure. Sutures, staples and adhesives have been used with varying levels of success. These prior techniques and the material and equipment used fail to minimize or limit the damage to the particular tissue and most importantly do not eliminate foreign body reactions of the patient to the added material. Specifically, the reaction of the patient's body is normally to surround the foreign body, i.e. added scar tissue, with barrier cells to thereby isolate the foreign matter from the normal cells within the patient. Consequently, the scar or evidence of the trauma is increased in size. The added material increases the cost of any surgical operation or procedure and post surgical concerns and healing.

Vascular tissue sealing and/or joining is important to the minimization of and/or elimination of bleeding or to the reconnection of tissue structures after surgical removal of undesirable organs or growths. Electrosurgery has been used to cut and coagulate tissue but the control needed to cleanly seal and/or join cut tissue and coagulate the bleeders has been lacking particularly in highly vascularized tissue, i.e. the particular patient tissue of interest and concern herein. Specifically, various approaches to coagulation, fulguration, cauterization for forming minimal and or flexible eschar over the bleeders have been tried. Different high frequency waveforms for coagulation by electrosurgical energy, argon gas enhanced coagulation and non sticking electrosurgical electrodes have been designed manufactured and sold with varying degrees of success at reducing healing time and the amount of evidence of surgical intrusion. All of the foregoing increases cost and complexity of surgical healing.

U.S. Pat. No. 4,043,342 has electrosurgical implements with sesquipolar electrode structures with active and return electrodes supported by insulated connectors respectively spring biased.

WO 9313719 has an electrosurgical instrument including a support structure with two electrodes interconnected with it to allow relative motion there between. A biasing device, such as a spring, urges the current return electrode into contact with tissue when the active electrode is positioned for surgery. The return electrode is longitudinally and laterally movable relative to the active electrode. A signal source provides a tissue cutting signal and a coagulation signal. The current return electrode has a tissue contact surface which defines a planar interface with the tissue during surgery. The active electrode is transversely movable relative to the interface. It increases contact surface to reduce likelihood of tissue damage and to easily control cutting depth. U.S. Pat. No. 5,047,027 has a bipolar electrosurgical instrument designed for resecting tumorous growths from the esophagus bladder or other internal organ wherein the site of the tumor is reached by way of an endoscope. The cutter is dimensioned to fit down the central lumen of the endoscope. An elongated flexible tube has a conductive helical spring cantilevered from the distal end of the tube, forming a return electrode and conductive wire hoop spaced a predetermined gap distance from the distal-most convolution of the helical spring and whose plane is perpendicular to the longitudinal axis of the flexible tube forms the active electrode.

Wires for applying a high frequency RF voltage across the electrodes extend through the lumen of the flexible tube. As the distal end portion of the instrument is dragged over the tumor to be resected, the cantilevered helical spring is laterally displaced, allowing the RF current leaving the active hoop electrode to cut through the tumorous tissue.

U.S. Pat. No. 5,007,908 has an instrument with an elongate flexible tubular member having a proximal end, a distal end and multiple lumens extending between them. Affixed to the distal end of the tube is a bullet-shaped ceramic tip member having a centrally-disposed longitudinal bore passing through the side wall of the tip member. The ceramic exterior surface of the tip member is covered with a conductive layer forming a first inactive electrode. An electrical conductor joined to that electrode surface feeds back through a lumen of the tube to its proximal end where it may be coupled to an electrosurgical generator. Also running a through a lumen in the tube is another conductor which can be made to project outwardly through the opening in the top member. A hub having a spring-loaded plunger is affixed to the proximal end of the tube with the plunger joined to the wire so that when the plunger is depressed the distal end of the wire will project a short distance beyond the extremity of the tip member. By coupling this second conductor to an electrosurgical generator, it becomes the active electrode of a bipolar pair.

U.S. Pat. No. 5,290,286 has an electrosurgical instrument with a bipolar pair of conductive electrodes for the cutting of tissue in which at least one electrode is moveable in relation to the other. The electrodes are mounted relative to an insulating plug, which is secured at the distal end of a tubular member. Pressure exerted on a thumb loop shifts the position of one electrode relative to the other. Upon application of RF voltage, the distance at which the electrodes are placed controls the amount of arcing which will occur between electrodes, when placed within a proper range. The electrodes are supplied with power from a standard RF energy source, controlled from a foot or hand switch. The insulating plug may further include metal traces disposed on the peripheral surface. When energized, these traces function as a bipolar pair of electrodes for effecting electrocoagulation of tissue and blood. The instrument is for insertion in laparoscopic trocar or endoscope for trimming small polyps from wall of colon and removal of tissue, and coagulating particular vascular tissue areas.

U.S. Pat. No. 5,342,357 has a cauterization system with a radio frequency energy source including a control unit connected to the energy source, and an electrosurgical probe. The probe has a handle with an elongate member extending from the handle. The distal end of the elongate member is tapered and includes a cauterization tip and a retractable cutting electrode. The probe includes a conduit for the transmission of cooling fluid to the distal end. The temperature of the electrode on the distal end of the probe is monitored and is used to control the rate of flow of the cooling fluid to the tip. A generator supplies electrical energy to the electrodes and the impedance of the tissue between the electrode is monitored to prevent tissue damage due to high temperatures. The system controls transfer of heat to tissue during surgery and prevents tissue or coagulant from welding to energy delivering electrode.

None of the aforementioned equipment has offered the surgeon the level of control needed to remodel and reform the tissue with electrosurgical energy. No mechanism for the application of clamping pressure, electrosurgical energy and temperature to seal and/or join vascularized tissue has been found. The tissue of the patient includes collagen which has been found to bind an injury or wound, surgical or otherwise, when subject to adequate pressure and temperature. Collagen can be melted and resolidified into a load resistant natural tissue coagulant so the reformed structure is capable of enduring loads similar to that carried by uncut tissue. No mechanism for the adequate and proper application of temperature and pressure is known.

A related patent application entitled "Energy Delivery System for Vessel Sealing", attorney docket number PC 9202, has been filed concurrently with this application.

SUMMARY OF THE INVENTION

A clamping force mechanism for a clamping electrosurgical instrument allows a user to seal and/or join particular vascular tissue of a patient. The clamping force mechanism is preferably elongate having user and a patient ends. An actuator may be at the user end and a pair of the end effectors might be at the patient end so the pair of end effectors when connected to the actuator operate from the user end to control the motion of the end effectors. The pair of end effectors may each have an opposing face of an area for contact with the particular vascular tissue of the patient.

A lost motion connection is most preferably in the preferred embodiment between the end effectors and the actuator to transfer user manipulation of the actuator to the end effectors and for maintaining predetermined clamping force applications during journey and/or sealing the particular vascular tissue of the patient. A yielding member may be included in the lost motion connection so the opposing faces clamp the particular tissue of the patient therebetween with force from the yielding member. The yielding member may in the preferred embodiment include a spring located near the actuator at the user end.

An elongated transfer rod in the lost motion connection is preferably between the spring near the actuator and the end effectors at the patient end for movement thereof between an open position for receiving the particular tissue of the patient to a clamping position for maintaining the predetermined force on the particular tissue of the patient between the end effectors. A locking linkage coupled to the actuator and the yielding member may retain the opposing faces held against the particular tissue of the patient therebetween with the force from the yielding member to achieve the predetermined force. Stepped latching positions on the actuator preferably permit the user to selectively set the locking linkage and the yielding member establishing different levels of force for the particular vascular tissue sealed to retain the set force in accord with the particular tissue being sealed. The stepped latching positions may be associated with different particular vascular tissue such as arteries or veins or mesentary.

An active electrode is most preferably carried on one of the end effectors. A return electrode can also contact the tissue of the patient. An electrosurgical energy supply connects across the active electrode and the return electrode to deliver electrosurgical energy between and across the active electrode and the return electrode when the particular tissue of the patient is held by the end effectors. The electrosurgical energy supply may include an electrosurgical generator.

A feedback circuit can be in the electrosurgical generator and in circuit with the active and the return electrodes to respond to parameters indicative of energy delivery through the particular vascular tissue of the patient interposed between the active and return electrodes.

A temperature sensor may also be in the feedback circuit and preferably carried on one of the opposed faces; the sensor to respond to the temperature of the particular vascular tissue of the patient between the opposed faces during delivery of electrosurgical energy. An impedance monitor in the feedback circuit can also be electrically hooked up to the electrosurgical generator to respond to the impedance changes of the particular vascular tissue of the patient between the active and return electrode during delivery of electrosurgical energy.

A control associated with the electrosurgical energy supply most preferably applies electrosurgical energy to the held particular tissue of the patient in response to the application of the predetermined force for the sealing the particular tissue between the end effectors.

Alternatively, in a bipolar circuit the return electrode could be on one of the pair of end effectors opposite the active electrode. Optionally, the return electrode might be on one of the pair of end effectors that carries the active electrode with an electrical insulator disposed between those active and the return electrodes. Similarly, the return electrode may be a pad connected to the tissue of the patient and this is a monopolar circuit.

The yielding member might be a hydraulic coupling as part of the lost motion connection between the end effectors. The hydraulic coupling can be located near the actuator. The yielding member could be a slip clutch within the lost motion connection near the actuator at the user end.

The pair of end effectors may have opposing faces each of an equal and preset area to clamp the particular tissue of the patient therebetween with the force from the yielding member so that a force is applied to the particular tissue in a preferred range.

A method allows a user to clamp and apply force and electrosurgical energy to seal and/or join particular vascular tissue of a patient with the clamping force mechanism for the instrument. The steps of the method may include transferring user manipulation of the actuator to the pair of end effectors with the lost motion connection, maintaining with the lost motion connection predetermined clamping force application during sealing of the particular tissue between the end effectors and applying electrosurgical energy for sealing the held particular tissue of the patient in response to the clamping thereof between the end effectors with a control associated with the electrosurgical energy supply.

The method step of applying electrosurgical energy can include responding to the parameter of the temperature of the particular tissue of the patient between the end effectors during delivery of electrosurgical energy with the feedback circuit including the temperature sensor carried on one of the opposed faces.

The method step of applying electrosurgical energy may be limited by the impedance of the particular tissue of the patient between the active and return electrodes during delivery of electrosurgical energy with the impedance monitor.

The method step of maintaining the predetermined clamping force during sealing of the particular tissue may be performed by shifting the yielding member so the opposing faces clamp the particular tissue of the patient therebetween with force from the yielding member.

The method step of shifting preferably secures the predetermined clamping force during sealing of the particular tissue by the resilient bias from the yielding member and by most preferably including the step of urging with the spring.

The method step of shifting could alternately secure the predetermined clamping force during sealing of the particular tissue by the yielding member with the step of moving the end effectors between their open position for receiving the particular tissue to the clamping position with the elongated transfer rod.

The method step of shifting with the actuator may secure the predetermined clamping force during sealing of the particular tissue of the patient by the resilient bias of the yielding member with the alternative step of urging with the hydraulic coupling.

The method step of shifting with the actuator can secure the predetermined clamping force during sealing of the particular tissue by the resilient bias of the yielding member with the step of urging with the slip clutch.

The method step of maintaining the predetermined clamping pressure during sealing particular tissue with the step of using the force from the yielding member so that pressures within a preferred range may be achieved with the locking linkage.

DETAILED DESCRIPTION OF THE INVENTION

Figure 1:
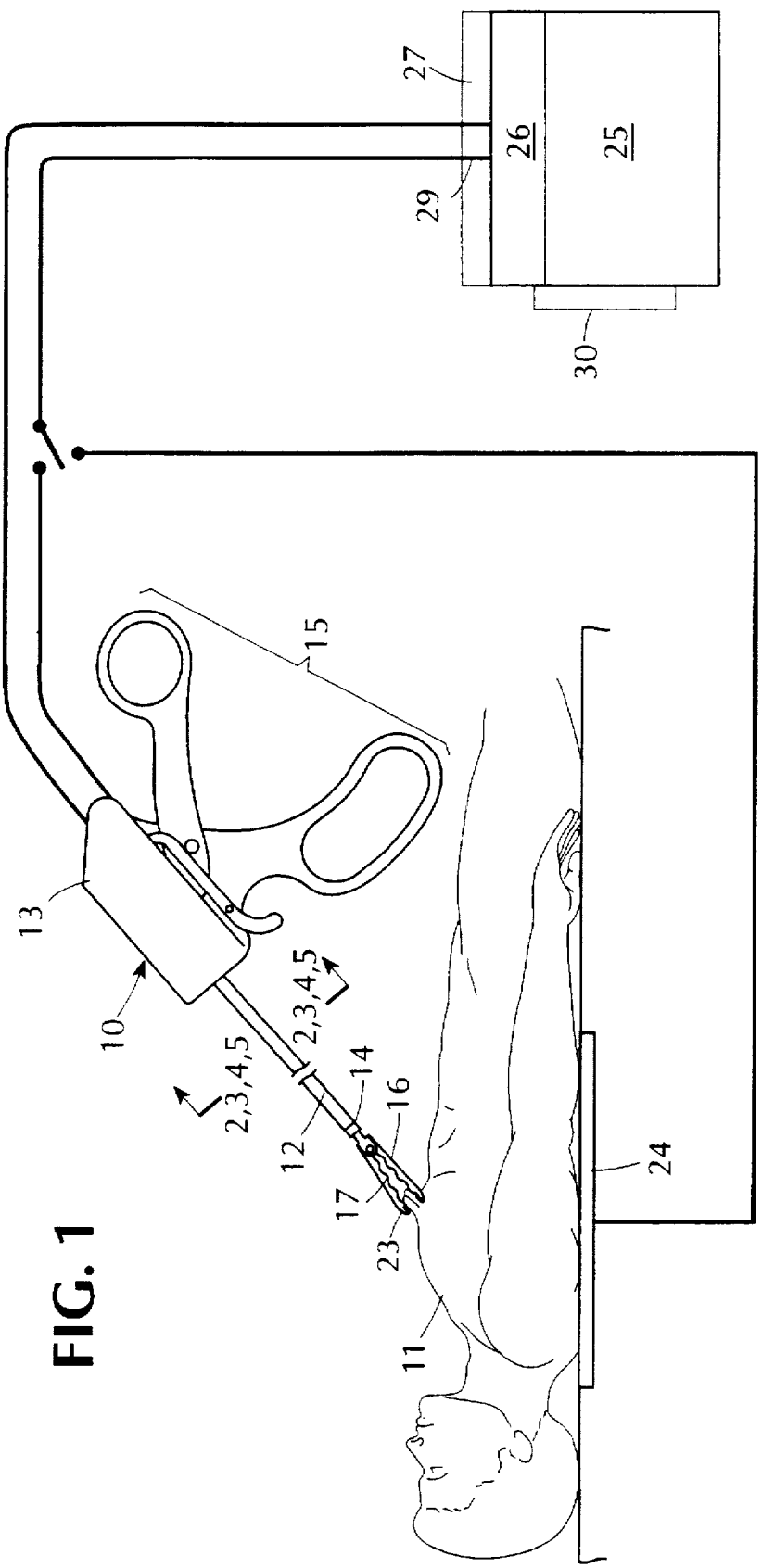
FIG. 1 is a schematic view of an electrosurgical supply and circuit for a clamping force mechanism to allow a user to apply force within a preferred range to hold particular vascular tissue of a patient during application of electrosurgical energy to seal and/or join the particular vascular tissue.

A clamping force mechanism 10 of an instrument allows a user to clamp and apply force and electrosurgical energy to seal and/or join particular vascular tissue of a patient 11, in FIG. 1. The clamping force mechanism 10 includes an elongate support 12 particularly good for endoscopic procedures having a user end 13 and a patient end 14. An actuator 15 is at the user end 13 or operation by the user. A pair of the end effectors 16 is at the patient end 14 and the pair of end effectors 16 connect to the actuator 15 for operation thereby and from the user end 13 to control the motion of the pair of end effectors 16. The pair of end effectors 16 each have an opposing face 17 of an area for contact with the particular tissue of the patient 11 as shown in FIGS. 2, 3, 4 and 5.

A lost motion connection 18 is positioned between the pair of end effectors 16 at the patient end 14 and the actuator 15 at the user end 13, in FIGS. 2, 3, 4 and 5. The lost motion connection 18 transfers user manipulation of the actuator 15 to the pair of end effectors 16 for maintaining a predetermined clamping force application during sealing the particular tissue of the patient 11 between the pair of end effectors 16. A yielding member 19 is in the loss motion connection 18 so the opposing faces 17 clamp the particular vascular tissue of the patient 11 therebetween with force from the yielding member 19. The yielding member 19 includes a spring 20, as part of the lost motion connection 18, between the pair of end effectors 16 at the patient end 14 and the actuator 15 at the user end 13. The spring 20 is located near the actuator 15 at the user end 13.

An elongated transfer rod 21 connected to the lost motion connection 18 is located between the spring 20 near the actuator 15 and the pair of end effectors 16 at the patient end 14, in FIGS. 2, 3, 4 and 5. The rod 21 couples to the pair of end effectors 16 for movement thereof between an open position in FIG. 2 for receiving the particular tissue of the patient 11 to a clamping position for maintaining the predetermined force on the particular tissue of the patient 11 between the pair of the end effectors 16.

Figure 2:
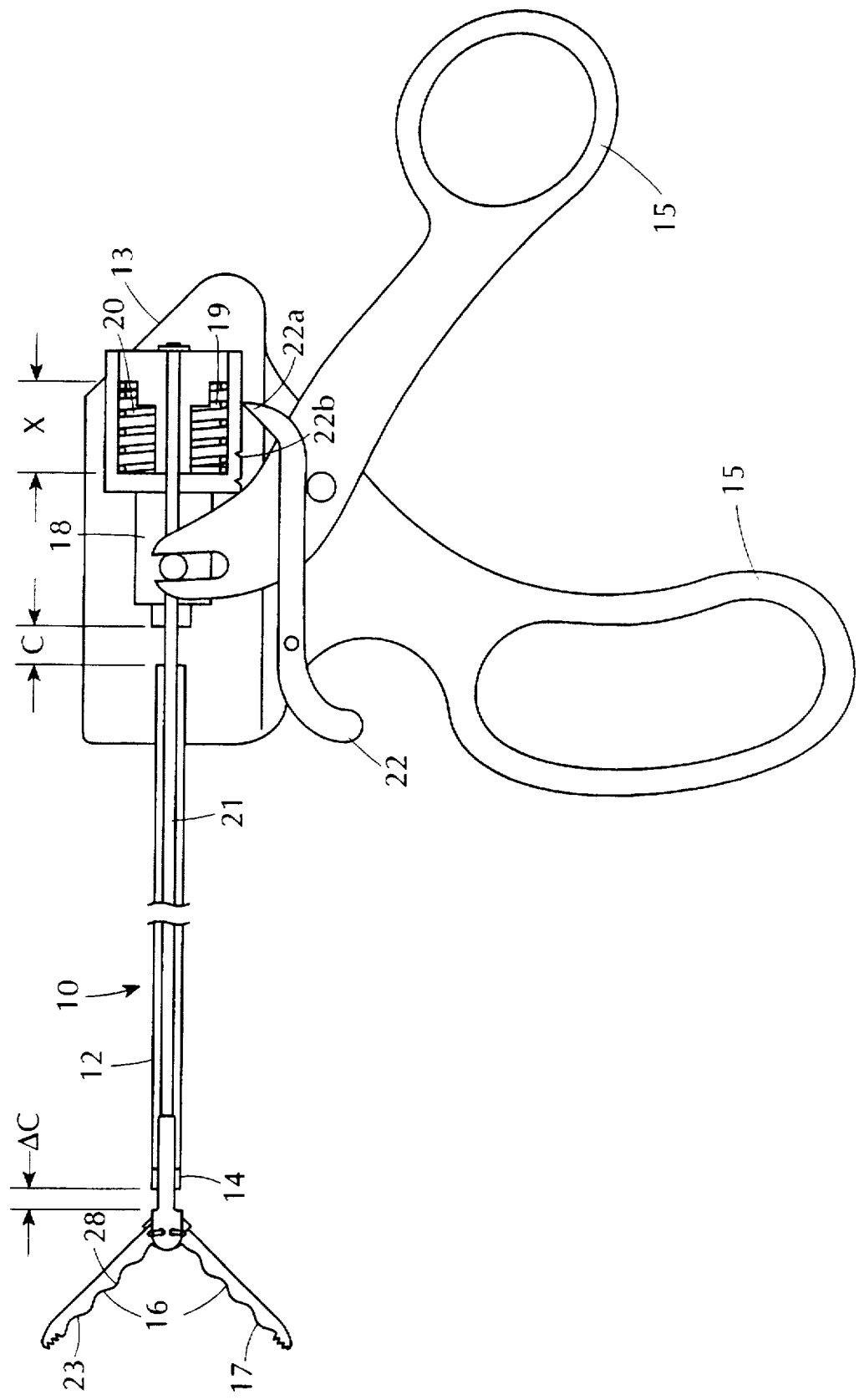
FIG. 2 is a side view in partial cross section taken along lines 2—2 of FIG. 1 and showing the clamping force mechanism wherein a spring is used as a lost motion connection between the user and end effectors shown herein in a fully open position.
Figure 3:
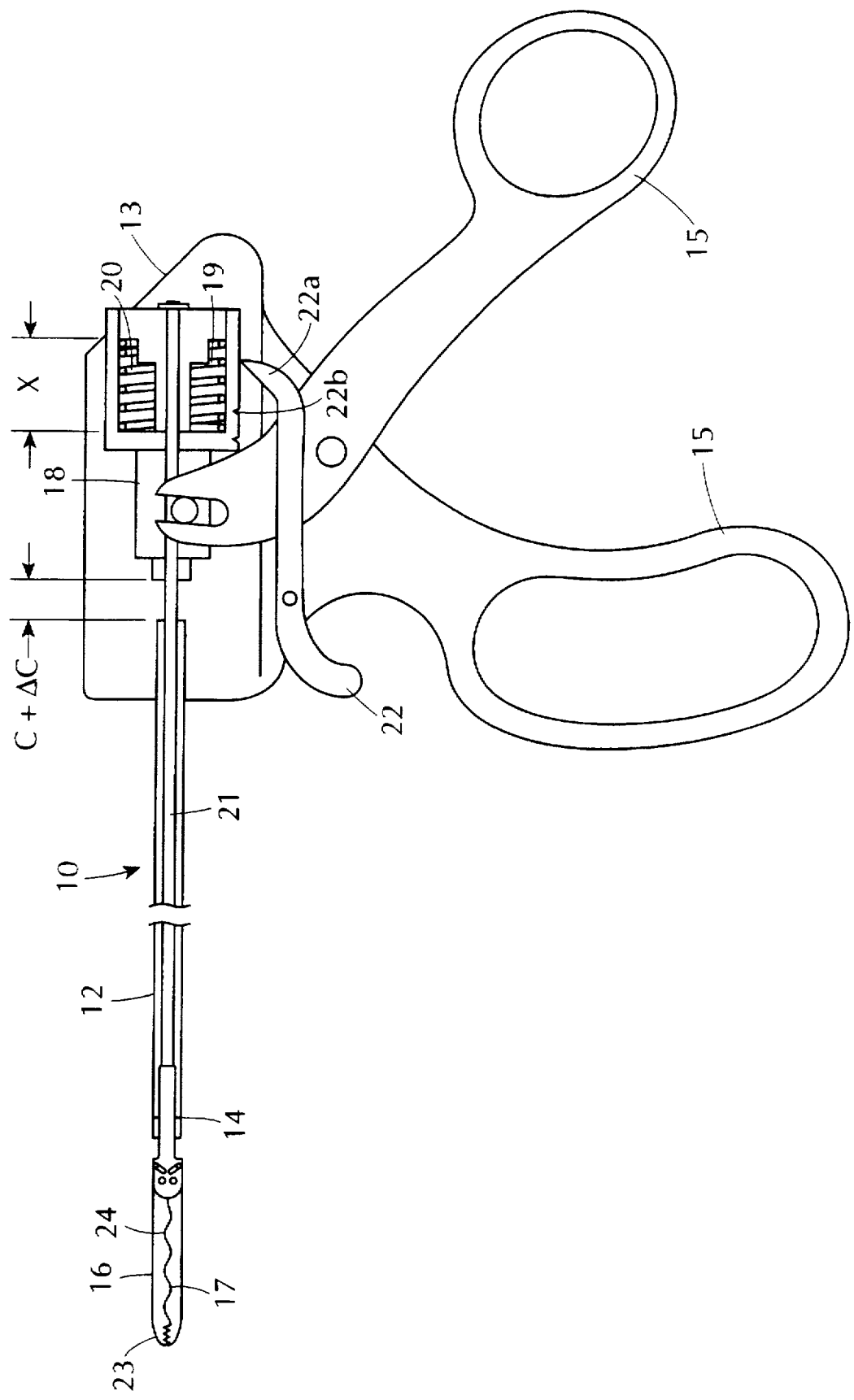
FIG. 3 is a side view in partial cross section taken along lines 3—3 of FIG. 1 and showing the clamping force mechanism wherein the end effectors are shown in closed position.
Figure 4:
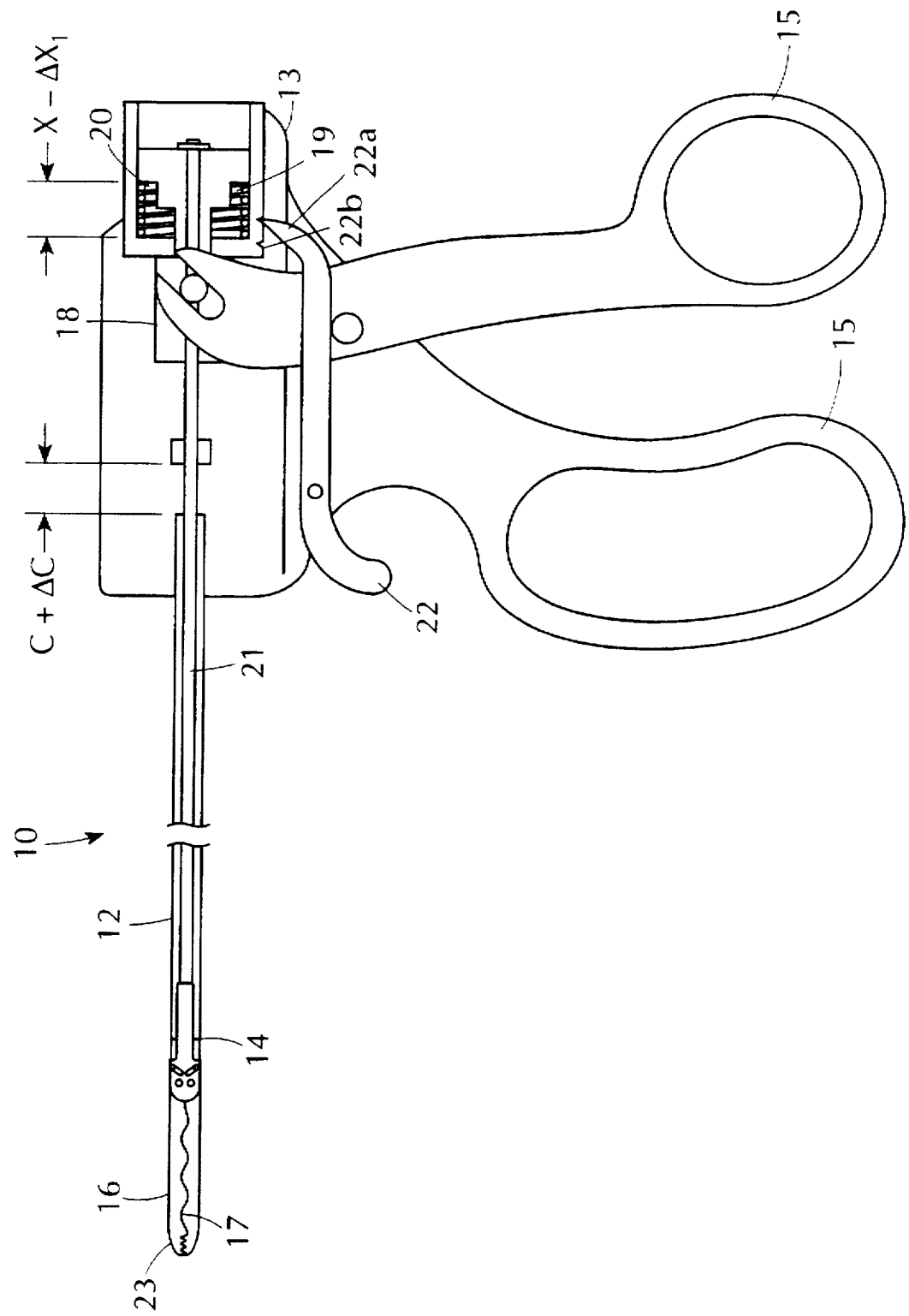
FIG. 4 is a side view in partial cross section taken along lines 4—4 of FIG. 1 and showing the clamping force mechanism wherein the end effectors are in partially compressed position.
Figure 5:
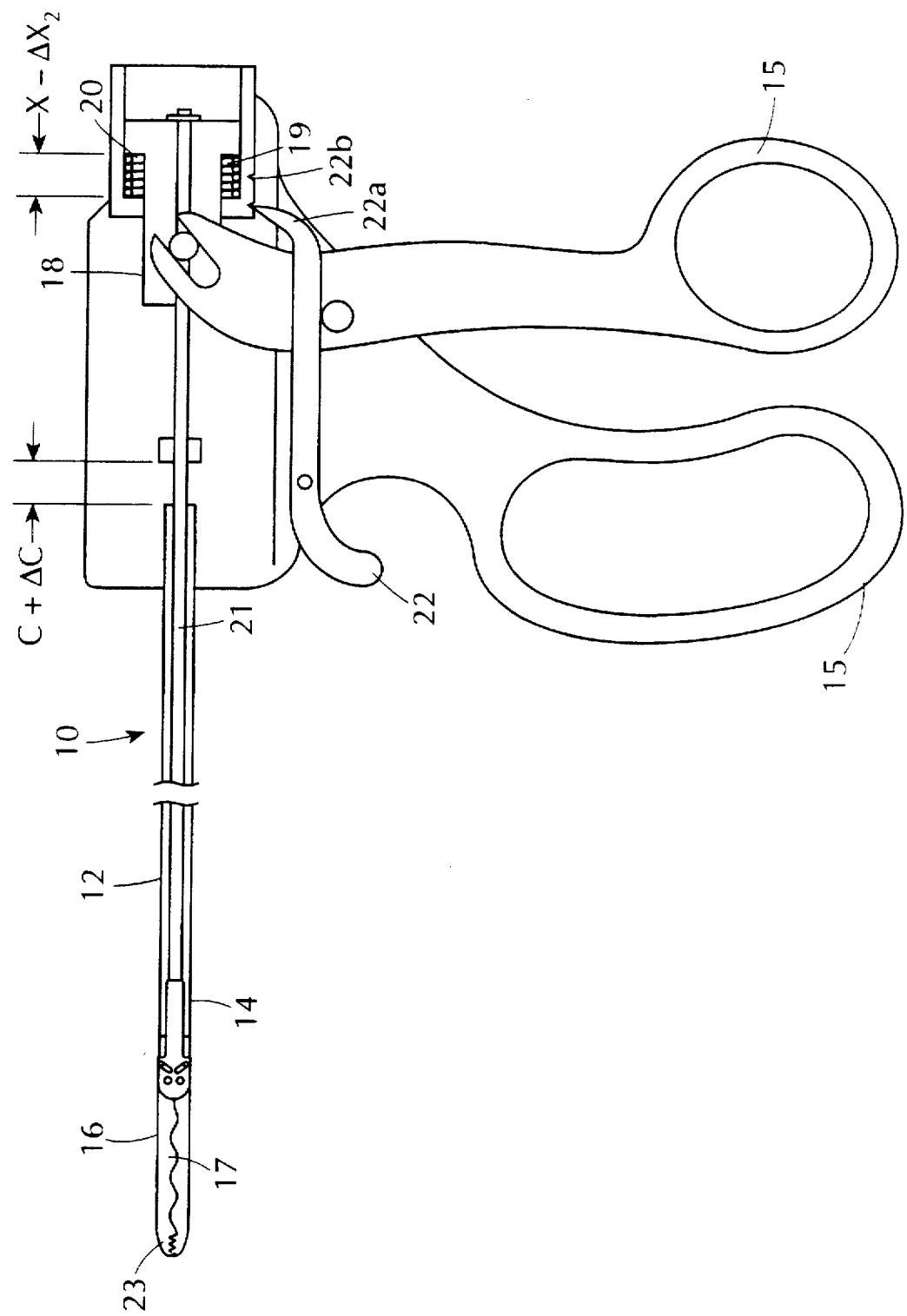
FIG. 5 is a side view in partial cross section taken along lines 5—5 of FIG. 1 and showing the clamping force mechanism wherein the end effectors are in the fully closed compressed position, actuator and the pain of end effectors.

In FIGS. 2, 3, 4 and 5, a locking linkage 22 coupled to the actuator 15 and the yielding member 19 retains the opposing faces 17 held against the particular tissue of the patient 11 therebetween with the force from the yielding member 19 to achieve predetermined forces of compression. FIGS. 3, 4 and 5 show different levels of compression, i.e. no force, partial compression and full compression. This is achieved with the catch 22a and notches 22b as shown but any form of stepped latching arrangement that would hold the actuator 15 in a preset position is acceptable. Stepped latching positions on the actuator 15 permit the user to selectively set the locking linkage 22 and the yielding member 19 establishing the force for the particular vascular tissue sealed to retain the predetermined force in accord with the particular vascular tissue being sealed. The stepped latching positions may be associated with different particular vascular tissue such as arteries or veins or mesentary if desired. For example, arteries will require a greater closure force than veins. It has been found that a closure force of greater than 1500 grams is effective for sealing arteries. A closure force of less than 500 grams is effective for sealing veins.

An active electrode 23 is carried on one of the pair of end effectors 16 in FIG. 1 but could be both of the end effectors 16. A return electrode 24 is in contact with the tissue of the patient 11. An electrosurgical energy supply 25 connects across the active electrode 23 of the pair of end effectors 16 and the return electrode 24. The electrosurgical energy supply 25 delivers electrosurgical surgery between and across the active electrode 23 and the return electrode 24 when the particular tissue of the patient 11 is held by the pair of end effectors 16. The electrosurgical energy supply 25 includes an electrosurgical generator 26.

A feedback circuit 27 is in the electrosurgical generator 26. The feedback circuit 27 is in circuit with the active electrode 23 and the return electrode 24 and is responsive to the parameters indicative of energy delivery through the particular tissue of the patient 11 interposed between the active electrode 23 and the return electrode 24.

A temperature sensor 28 in FIG. 2 is connected to the feedback circuit 27 is carried on one of the opposed faces 17 and responds to the parameter of temperature of the particular tissue of the patient 11 between the pair of end effectors 16 during delivery of electrosurgical energy. An impedance monitor 29 in the feedback circuit 27 is electrically hooked up to the electrosurgical generator 26. The impedance monitor 29 responds to the parameter of the impedance of the particular tissue of the patient 11 between the active electrode 23 and return electrode 24 during delivery of electrosurgical energy.

A control 30 in FIG. 1 associated with the electrosurgical energy supply 25 applies electrosurgical energy to the held particular tissue of the patient 11 in response to the application of the predetermined force for the sealing the particular tissue between the pair of end effectors 16.

The return electrode 24 is alternatively shown in FIG. 1 on one of the pair of end effectors 16 opposite the active electrode 23. The return electrode 24 when on the one of the pair of end effectors 16 that carries the active electrode has an electrical insulator elongated transfer rod 21 disposed between the active electrode and the return electrode shown in FIG. 3. The return electrode is specifically a pad connected to the tissue of the patient 11 in shown FIG. 1.

Figure 6:
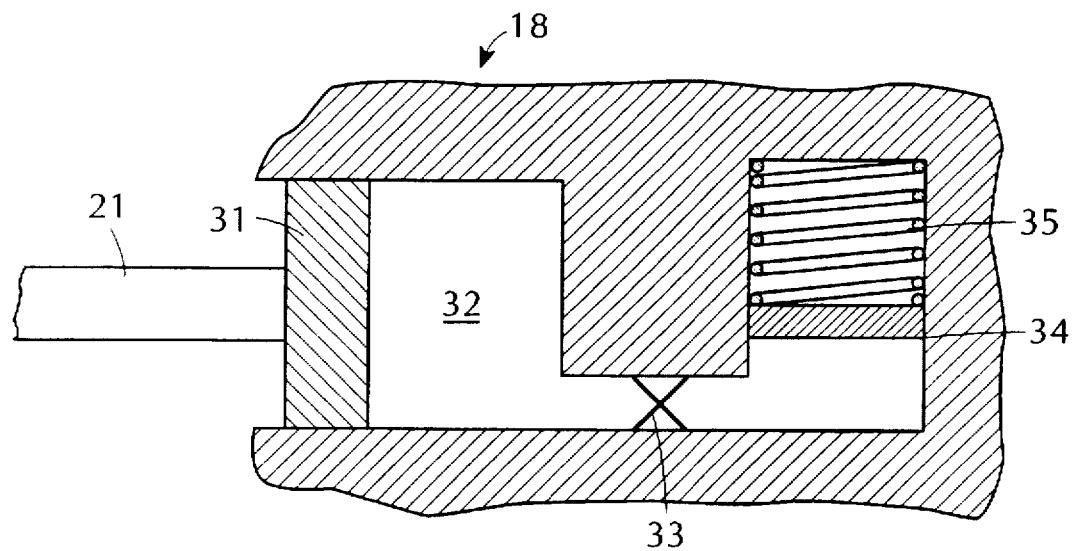
FIG. 6 is a partial schematic view of the hydraulic coupling for the lost motion connection.

The yielding member 19 can be a hydraulic coupling best shown in FIG. 6 as part of the lost motion connection 18 and is located between the pair of end effectors 16 at the patient end 14 and the actuator 15 at the user end 13. The hydraulic coupling is preferably located near the actuator 15 at the user end 13 but can be anywhere. The hydraulic coupling can include piston 31 attached to elongate transfer rod 21. Fluid is compressed and metered by valve 33 to a floating plug 34 which is loaded by a spring 35 thus the compressive nature of fluid is primarily used to add the resilient bias.

Figure 7:
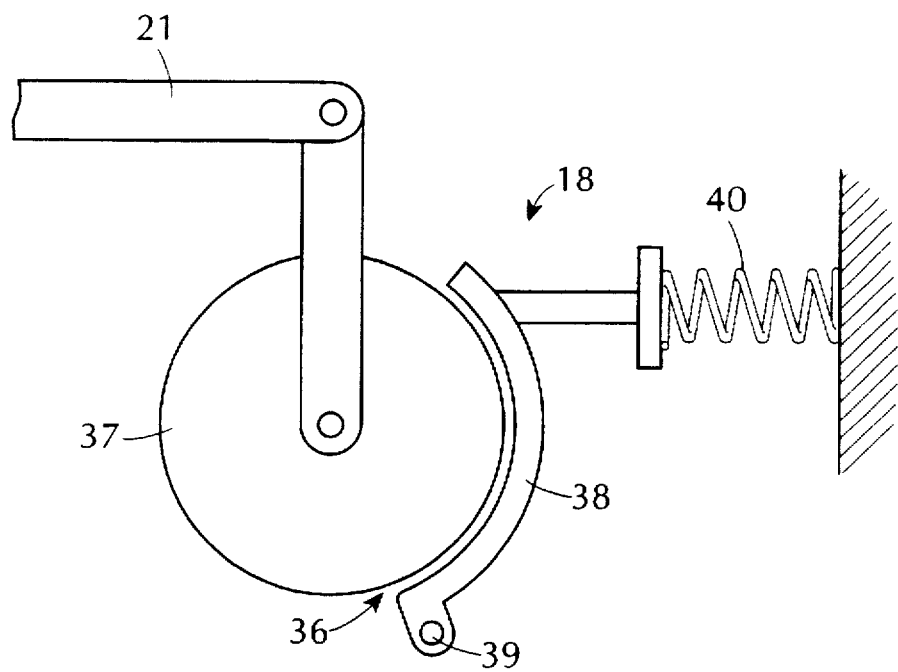
FIG. 7 is a partial schematic view of the slip clutch for the lost motion connection.

The yielding member 19 could alternatively be a slip clutch 36 within the lost motion connection 18 located between the pair of end effectors 16 at the patient end 14 and the actuator 15 at the user end 13 as shown in FIG. 7. The slip clutch 36 is most preferably located near the actuator 15 at the user end but could be elsewhere.

The slip clutch 36 in FIG. 7 is connected to elongate transfer rod 21 and includes a wheel 37 journalled to rotated when the rod 21 reciprocates. There is a brake band 38 pivotally mounted at pivot 39 to be rotated against the wheel 37. The function connection between the wheel 37 and the brake band 38 acts as the yielding member 19 in this slip clutch 36. Although a spring 40 is shown the yielding is primarily the friction load of the brake.

The pair of end effectors 16 have opposing faces each of an equal and preset area. The opposing faces clamp the particular tissue of the patient 11 therebetween as seen in FIG. 1 with the force from the yielding member 19 so that a preferred pressure is applied to the particular tissue.

A method allows a user to clamp and apply force and electrosurgical energy to seal and/or join particular vascular tissue of a patient 11 with the clamping force mechanism 10 of the instrument hereinbefore described. The steps of the method including transferring user manipulation of the actuator 15 to the pair of end effectors 16 with the lost motion connection 18, maintaining a predetermined clamping force application during sealing and/or joining of the particular tissue of the patient 11 between the pair of end effectors 16 with the lost motion connection 18 and applying electrosurgical energy for sealing and/or joining the held particular tissue of the patient 11 in response to the clamping thereof between the pair of end effectors 16 with the control associated with the electrosurgical energy supply 25.

The method step of applying electrosurgical energy includes responding to the parameter of the temperature of the particular tissue of the patient 11 between the pair of end effectors 16 during delivery of electrosurgical energy with the feedback circuit 26 including the temperature sensor 28 carried on one of the opposed faces 17.

The method step of applying electrosurgical energy includes responding to the impedance of the particular tissue of the patient 11 between the active electrode and return electrode during delivery of electrosurgical energy with the impedance monitor 27.

The method step of maintaining the predetermined clamping force application during sealing and/or joining of the particular tissue of the patient 11 by shifting of the yielding member 19 in the lost motion connection 18 with the actuator 15 so the opposing faces clamp the particular tissue of the patient 11 therebetween with force from the yielding member 19.

The method step of shifting with the actuator 15 secures the predetermined clamping force application during sealing of the particular tissue of the patient 11 by the resilient bias of the yielding member 19 and by including the step of urging with the spring 20.

The method step of shifting with the actuator 15 secures the predetermined clamping force application during sealing of the particular tissue of the patient 11 by the yielding member 19 and by including the step of moving the pair of end effectors 16 between their open position for receiving the particular tissue of the patient 11 to the clamping position with the elongated transfer rod 21 located between the spring 20 near the actuator 15 and the pair of end effectors 16 at the patient end 14.

The method step of shifting with the actuator 15 secures the predetermined clamping force application during sealing of the particular tissue of the patient 11 by the resilient bias of the yielding member 19 and by including the step of urging with the hydraulic coupling as part thereof.

The method step of shifting with the actuator 15 secures the predetermined clamping force application during sealing of the particular tissue of the patient 11 by the resilient bias of the yielding member 19 and by including the step of urging with the slip clutch 36 as part thereof.

The method step of maintaining the predetermined clamping force application during sealing of the particular tissue of the patient 11 and by the step of using the force from the yielding member 19 so that pressure is applied to the particular tissue.

What is claimed is:

1. A clamping force mechanism for an instrument for allowing a user to clamp and apply force and electrosurgical energy to seal and/or join particular vascular tissue of a patient comprising:

an elongate support having a user end and a patient end;

an actuator at the user end for operation by the user;

a pair of end effectors at the patient end, at least one of the pair of end effectors connected to the actuator for operation thereby and from the user end to control relative motion between the pair of end effectors, the pair of end effectors each having an opposing face of an area adapted to be used for contact with particular tissue of the patient;

a lost motion connection between at least one of the pair of end effectors at the patient end and the actuator at the user end, the lost motion connection for transferring user manipulation of the actuator to at least one of the pair of end effectors for maintaining a predetermined clamping force within an preferred range irrespective of total user manipulation over the opposing face of an area during sealing of particular tissue of the patient between the pair of end effectors;

an active electrode carried on one of the pair of end effectors;

a return electrode adapted to be in contact with the tissue of the patient for forming an electrosurgical circuit between the active and return electrodes;

an electrosurgical energy supply connected across the active electrode of the pair of end effectors and the return electrode, the electrosurgical energy supply for delivery of electrosurgical energy through the electrosurgical circuit between and across the active electrode and the return electrode when particular tissue of the patient is held by the pair of end effectors; and a control associated with the electrosurgical energy supply adapted to apply electrosurgical energy to particular tissue of the patient that is held in response to application of the predetermined clamping force for sealing particular tissue between the pair of end effectors.

2. The clamping force mechanism of claim 1 wherein the lost motion connection between the actuator and the pair of end effectors includes a yielding member, and the opposing faces adapted to clamp particular tissue of the patient therebetween with the predetermined clamping force from the yielding member over the opposing face of an area to achieve the predetermined clamping force during clamping and while sealing.

3. The clamping force mechanism of claim 2 wherein a locking linkage coupled to the actuator and the yielding member retains the opposing faces adapted to be held against particular tissue of the patient therebetween with the predetermined clamping force from the yielding member over the opposing face of an area to achieve the predetermined clamping force.

4. The clamping force mechanism of claim 3 wherein stepped latching positions on the actuator permit the user to selectively set the locking linkage coupled therewith so the yielding member establishes the selected predetermined clamping force over the opposing face of an area relative to particular vascular tissue sealed to retain the predetermined clamping force in accord with particular tissue being sealed.

5. The clamping force mechanism of claim 1 wherein the electrosurgical energy supply includes an electrosurgical generator having a feedback circuit in circuit with the active electrode and the return electrode, the feedback circuit responsive to energy delivery across particular tissue of the patient interposed between the pair of end effectors.

6. The clamping force mechanism of claim 5 wherein the feedback circuit includes an impedance monitor, the impedance monitor electrically hooked up to the electrosurgical generator, an impedance circuit responsive to impedance of particular tissue of the patient between the active electrode and return electrode during delivery of electrosurgical energy.

7. The clamping force mechanism of claim 5 wherein the feedback circuit includes a temperature sensor carried on one of the pair of end effectors, the temperature sensor is responsive to temperature of particular tissue of the patient between the pair of end effectors during delivery of electrosurgical energy.

8. The clamping force mechanism of claim 2 wherein the yielding member is a spring as part of the lost motion connection between the pair of end effectors at the patient end.

9. The clamping force mechanism of claim 8 wherein the yielding member is at the actuator at the user end, the spring located near the actuator at the user end.

10. The clamping force mechanism of claim 8 wherein the lost motion connection includes an elongated transfer rod between the spring near the actuator and the pair of end effectors at the patient end, the rod coupled to the pair of end effectors for movement thereof between an open position adapted for receiving particular tissue of the patient to a clamping position for maintaining the predetermined clamping force on particular tissue of the patient between the pair of end effectors.

11. The clamping force mechanism of claim 1 wherein the return electrode is on one of the pair of end effectors opposite the active electrode.

12. The clamping force mechanism of claim 1 wherein the return electrode is on one of the pair of end effectors that carries the active electrode and an electrical insulator is disposed between the active electrode and the return electrode.

13. The clamping force mechanism of claim 1 wherein the return electrode is a pad adapted to be connected to particular tissue of the patient.

14. The clamping force mechanism of claim 2 wherein the yielding member is a hydraulic coupling as part of the lost motion connection between the pair of end effectors at the patient end 14 and the actuator at the user end, the hydraulic coupling located near the actuator at the user end.

15. The clamping force mechanism of claim 2 wherein the yielding member is a slip clutch within the lost motion connection between the pair of end effectors at the patient end and the actuator at the user end, the slip clutch located near the actuator at the user end.

16. The clamping force mechanism of claim 2 wherein the pair of end effectors have the opposing face of an area with each opposing face of an area having an equal and preset area, the actuator applies a first force adapted to grip particular tissue of the patient therebetween and the actuator when advanced by the user applies a second greater predetermined clamping force from the yielding member so that pressure is applied to particular tissue to clamp between the opposing faces with closure force in a range of 300 to 2500 grams.

17. A clamping force mechanism for an instrument for allowing a user to clamp and apply force and electrosurgical energy to seal and/or join particular vascular tissue of a patient comprising:

an elongate support having a user end and a patient end;

an actuator at the user end for operation by the user;

a pair of end effectors at the patient end, the pair of end effectors connected to the actuator for operation thereby and from the user end to control motion of the pair of end effectors, the pair of end effectors each having an opposing face of an area adapted for contact with particular vascular tissue of the patient;

a lost motion connection between the pair of end effectors at the patient end and the actuator at the user end, the lost motion connection for transferring user manipulation of the actuator to the pair of end effectors for maintaining force over the opposing face of an area to achieve a predetermined clamping force application during sealing of particular vascular tissue of the patient between the pair of end effectors;

a yielding member in the lost motion connection so the opposing faces clamp particular vascular tissue of the patient therebetween with the predetermined clamping force from the yielding member, the yielding member including a spring as part of the lost motion connection between the pair of end effectors at the patient end and the actuator at the user end, the spring located near the actuator at the user end to maintain a predetermined clamping force within an preferred range irrespective of total user manipulation;

an elongated transfer rod in the lost motion connection, the elongate transfer rod located between the spring near the actuator and the pair of end effectors at the patient end, the rod coupled to the pair of end effectors for movement thereof between an open position adapted to receive particular vascular tissue of the patient to a clamping position adapted to maintain the predetermined clamping force on particular vascular tissue of the patient between the pair of end effectors;

an active electrode carried on one of the pair of end effectors;

a return electrode in contact with the tissue of the patient;

an electrosurgical energy supply connected across the active electrode of the pair of end effectors and the return electrode to provide an electrosurgical circuit therebetween, the electrosurgical energy supply for delivery of electrosurgical energy between and across the active electrode and the return electrode when particular vascular tissue of the patient is held by the pair of end effectors;

an electrosurgical generator in the electrosurgical energy supply to provide electrosurgical energy;

a feedback circuit in the electrosurgical generator, the feedback circuit electrically coupled in circuit with the active electrode and the return electrode, the feedback circuit responsive to energy delivery through the electrosurgical circuit of particular vascular tissue of the patient interposed between the active electrode and the return electrode;

a temperature sensor in the feedback circuit, the temperature sensor carried on at least one of the opposed faces, the temperature sensor responding to temperature of particular vascular tissue of the patient between the pair of end effectors during delivery of electrosurgical energy;

an impedance monitor in the feedback circuit, the impedance monitor electrically hooked up to the electrosurgical generator, an impedance circuit responsive to impedance of particular vascular tissue of the patient between the active electrode and return electrode during delivery of electrosurgical energy, and a control associated with the electrosurgical energy supply adapted to apply electrosurgical energy to the particular vascular tissue of the patient that is held in response to the predetermined clamping force application for sealing particular vascular tissue between the pair of end effectors.

* * * * *